United States Patent
Shen et al.

(10) Patent No.: US 8,658,811 B2
(45) Date of Patent: Feb. 25, 2014

(54) PROCESS FOR THE PREPARATION OF DOCETAXEL, ITS INTERMEDIATES, AND METHODS FOR PREPARATION THEREOF

(75) Inventors: Xin Shen, Shanghai (CN); Huaxing Zhan, Shanghai (CN); Jidong Yang, Shanghai (CN); Xiao He, Shanghai (CN); Fuxing Lin, Shanghai (CN); Shaohong Wu, Shanghai (CN)

(73) Assignee: Shanghai Parling Pharma-Tech. Co., Ltd., Shanghai (CN)

( * ) Notice: Subject to any disclaimer, the term of this patent is extended or adjusted under 35 U.S.C. 154(b) by 739 days.

(21) Appl. No.: 12/741,714

(22) PCT Filed: May 22, 2009

(86) PCT No.: PCT/CN2009/071939
§ 371 (c)(1),
(2), (4) Date: May 6, 2010

(87) PCT Pub. No.: WO2010/057378
PCT Pub. Date: May 27, 2010

(65) Prior Publication Data
US 2010/0311991 A1 Dec. 9, 2010

(30) Foreign Application Priority Data
Nov. 19, 2008 (CN) .......................... 2008 1 0202997

(51) Int. Cl.
*C07D 407/00* (2006.01)
*C07D 493/00* (2006.01)

(52) U.S. Cl.
USPC .......................................... 549/510; 549/511

(58) Field of Classification Search
USPC .................................................. 549/510, 511
See application file for complete search history.

(56) References Cited

U.S. PATENT DOCUMENTS

| | | | | |
|---|---|---|---|---|
| 5,476,954 A | * | 12/1995 | Bourzat et al. | 549/510 |
| 5,616,739 A | * | 4/1997 | Mas et al. | 549/510 |
| 5,629,433 A | * | 5/1997 | Zheng et al. | 549/510 |
| 6,362,217 B2 | * | 3/2002 | Kadow et al. | 514/449 |
| 6,753,345 B2 | * | 6/2004 | Murray et al. | 514/449 |
| 7,202,370 B2 | * | 4/2007 | Naidu | 549/510 |

OTHER PUBLICATIONS

Kudyba et al DN 140:841479 RN 640279-68-1 (2003).*
Jagtap eta l Tetra. Let. 40 (1999) pp. 189-192.*

* cited by examiner

*Primary Examiner* — Andrew D Kosar
*Assistant Examiner* — Raymond Covington
(74) *Attorney, Agent, or Firm* — Lowe Hauptman & Ham, LLP

(57) ABSTRACT

Described is a process for preparing docetaxel 1, including the following steps: a) hydroxyl acylation reaction of compound 2 and 3 to obtain compound 4; b) deprotection group $R_1$ of the hydroxyl group of compound 4 obtained from step a to prepare compound 5; c) removing one tert-butoxycarbonyl of compound 5 obtained from step b to prepare compound 6; d) removing one acetyl of compound 6 obtained from step c to prepare compound 1; wherein, $R_1$ represents tert-butyl dimethyl silyl, triethylsilyl, ethoxyethyl, tetrahydropyranyl, trichloroethoxycarbonyl or methoxymethyl, Boc is tert-butoxycarbonyl, Ac is acetyl, and Ph is phenyl. Also disclosed are intermediates of docetaxel and methods for preparation thereof.

20 Claims, 2 Drawing Sheets

PROCESS FOR THE PREPARATION OF DOCETAXEL, ITS INTERMEDIATES, AND METHODS FOR PREPARATION THEREOF

The present application is national phase of PCT/CN2009/071939 filed May 22, 2009, and claims priority from Chinese Application Number 200810202997.3 filed Nov. 19, 2008, the disclosures of which are hereby incorporated by reference herein in their entirety.

FIELD OF THE INVENTION

The present invention relates to the process for preparing one anticancer medicine, its intermediate and methods for preparation thereof, specifically relates to a process for preparing docetaxel, its intermediates and methods for preparation thereof.

BACKGROUND OF THE INVENTION

Docetaxel (1) is obtained by the structure modification based on the paclitaxel. The docetaxel promises a broad range of anti-leukemic and tumor-inhibiting activity, and has been considered one of the most effective anticancer drugs till now, with the anticancer activity 1.3- to 12-fold more potent than paclitaxel. Docetaxel has the same complex structure as paclitaxel, including various function groups and chiral centers, which lead to great difficulty of the total synthesis. Semi-synthesis is the most effective chemical method for preparing docetaxel.

Figure 1:
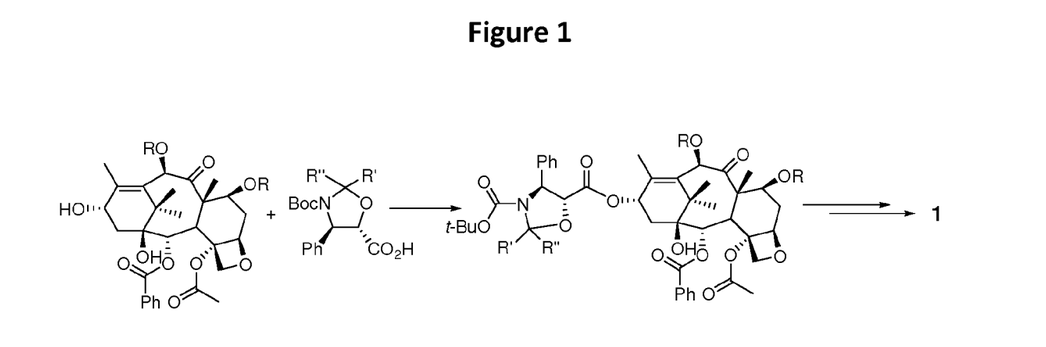
FIG. 1 shows a schema for making compound 1.
Figure 2:
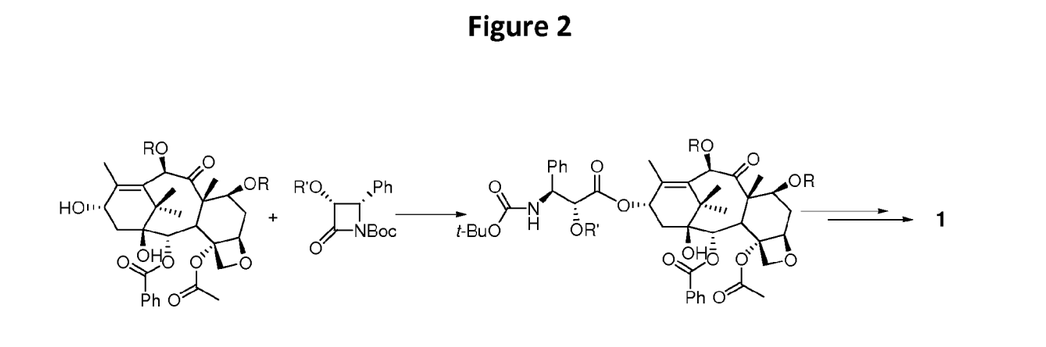
FIG. 2 shows a schema for making compound 1.

The semi-synthesis method reported in the references and patents may be divided into two categories. The first is that following the condensation reactions of protected 10-deacetylbaccatin III and five-membered oxazolidine side chain, the compound is de-protected through hydrolyzing to yield docetaxel. (U.S. Pat. No. 6,900,342); the second is that following the coupling reactions of protected 10-deacetyl-baccatin III with β-lactam under extremely low temperature in the presence of strong base (such as n-butyllithium), the compound is de-protected through hydrolyzing to yield docetaxel. (See the following scheme in FIGS. 1-2.)

In the first method (see FIG. 1), the condensation condition is milder, but a great amount of condensation reagent DCC (N,N'-dicyclohexyl carbodiimide) will be used and cause many difficulties in the following purification.

In the second method (see FIG. 2), the condition is more rigorous, because of the using of strong base, mishandling will cause decomposition of the protected 10-deacetylbaccatin III and waste of the expensive raw material. Moreover, the excessive side chain needed in this method not only increases the difficulty of the following purification, but also increases the cost of manufacture.

SUMMARY OF THE INVENTION

It is an object of the present invention to provide a process for preparing docetaxel, its intermediates and methods for preparation thereof, which solves the technical problem of the difficulty of purification, the waste of raw material, and the higher cost of manufacture in the known method of preparing docetaxel. In the methods for preparation of the present invention, the protective groups used are easy to be removed, the purification of the intermediates is easy, the cost is lower, the yield and the purity are higher, and the processes can be scaled to commercial implementation.

The present invention relates to a process for preparing docetaxel (Formular 1), including the following steps: compound 1 was prepared from compound 6 by removing one acetyl group.

Wherein, Boc is tert-butoxycarbonyl, Ac is acetyl, Ph is phenyl.

Wherein, the method and condition of deacetylation described can be the common method and condition of deacetylation in the field. Preferably, the deacetylation of compound 6 is performed via the action of hydrogen peroxide and sodium bicarbonate in organic solvent. Wherein, the organic solvent is preferably one or several chosen from dichloromethane, ethyl acetate, toluene, diethyl ether, isopropyl ether, acetone, acetonitrile and tetrahydrofuran. Tetrahydrofuran is more preferably used. The volume/mass ratio of solvent and compound 6 is preferably 5~50 ml/g. The sodium bicarbonate is preferably utilized in the form of 0.5%~saturated aqueous solution, more preferably saturated sodium bicarbonate aqueous solution. The usage of sodium bicarbonate is preferably 2~10 folds of the molar value of compound 6, more preferably 3~5 folds. Hydrogen peroxide is preferably utilized in the form of hydrogen peroxide aqueous solution, its mass percentage is preferably 10~70%, more preferably 30%. The usage of hydrogen peroxide is preferably 2~10 folds of the molar value of compound 6, more preferably 3~5 folds. The reaction is performed preferably at temperature between 0 and 50° C., more preferably at temperature between 20 and 35° C. The reaction time is preferably decided by detection of the completion of the reaction, usually 12~24 hours.

The present invention also relates to an intermediate compound 6 of docetaxel, wherein, Boc is tert-butoxycarbonyl, Ac is acetyl, and Ph is phenyl.

The present invention further relates to a process for preparing compound 6, including the following steps: compound 6 was prepared from compound 5 by removing one tert-butoxycarbonyl (Boc) group.

Wherein, Boc is tert-butoxycarbonyl, Ac is acetyl, and Ph is phenyl.

Wherein, the method and condition of removing one tert-butoxycarbonyl group described can be the common method and condition of removing one tert-butoxycarbonyl group connecting with nitrogen in the field. Preferably, the deprotection of compound 5 is performed via the action of trifluoroacetic acid in organic solvent. Wherein, the organic solvent is preferably one or several chosen from dichloromethane, ethyl acetate, toluene, diethyl ether, isopropyl ether, acetone, acetonitrile, and tetrahydrofuran. Dichloromethane is more preferably used. The volume/mass ratio of the solvent and compound 5 is preferably 5~20 ml/g. The usage of trifluoroacetic acid is preferably 0.1~2 folds of the molar value of compound 5, more preferably 0.2~0.5 folds. The reaction is performed preferably at the temperature between 0 and 50° C., more preferably at the temperature between 20 and 35° C. The reaction time is preferably decided by detection of the completion of the reaction, usually 1~8 hours.

The present invention also relates to an intermediate compound 5 of docetaxel, wherein, Boc is tert-butoxycarbonyl, Ac is acetyl, and Ph is phenyl.

The present invention further relates to a process for preparing compound 5, including the following steps: compound 5 is prepared from compound 4 by removing protection group $R_1$ of the hydroxyl group.

Wherein, $R_1$ represents tert-butyl dimethyl silyl (TBS), triethylsilyl (TES), ethoxyethyl (EE), tetrahydropyranyl (THP), trichloroethoxycarbonyl (Troc) or methoxymethyl (MOM), trichloroethoxycarbonyl (Troc) or triethylsilyl (TES) is preferable.

Wherein, the method and condition of removing protection group of the hydroxyl group described can be the common method and condition of protection group of the hydroxyl group in the field.

Preferably, where $R_1$ is trichloroethoxycarbonyl (Troc), the deprotection of compound 4 is performed via the action of acetic acid and zinc in organic solvent and water. Wherein, the organic solvent is preferably one or several chosen from dichloromethane, ethyl acetate, toluene, diethyl ether, isopropyl ether, acetone, acetonitrile, tetrahydrofuran, methanol, and ethanol. Methanol is more preferably used. The volume/mass ratio of the organic solvent and compound 4 is preferably 5~20 ml/g. The usage of acetic acid is preferably 5~20 folds of the molar value of compound 4, more preferably 5~6 folds. The zinc is preferably utilized in the form of zinc powder, the usage of which is preferably 2~20 folds of the molar value of compound 4, more preferably 3~5 folds. The reaction is performed preferably at temperature between 0 and 80° C., more preferably at temperature between 50 and 70° C. The reaction time is preferably decided by detection of the completion of the reaction, usually 2~12 hours.

Where $R_1$ is triethylsilyl (TES), the deprotection of compound 4 is performed via the action of tetrabutylammonium fluoride in organic solvent. Wherein, the organic solvent is preferably one or several chosen from dichloromethane, ethyl acetate, toluene, diethyl ether, isopropyl ether, acetone, acetonitrile, tetrahydrofuran, methanol, and ethanol. Tetrahydrofuran is more preferably used. The volume/mass ratio of the solvent and compound 4 is preferably 5~20 ml/g. The usage of tetrabutylammonium fluoride is preferably 1~20 folds of the molar value of compound 4, more preferably 1.2~2 folds. The reaction is performed preferably at temperature between 0 and 80° C., more preferably at temperature between 0 and 10° C. The reaction time is preferably decided by detection of the completion of the reaction, usually 5~24 hours.

Where $R_1$ is tert-butyl dimethyl silyl (TBS), the deprotection of compound 4 is performed via action of tetrabutylammonium fluoride in organic solvent, wherein, the reaction condition is the common condition of this method.

Where $R_1$ is ethoxyethyl (EE), the deprotection of compound 4 is performed via the action of diluted acid in solvent of alcohol and water, wherein, the reaction condition is the common condition of this method.

Where $R_1$ is tetrahydropyranyl (THP), the deprotection of compound 4 is performed via the action of diluted acid in solvent of alcohol and water, wherein, the reaction condition is the common condition of this method.

Where $R_1$ is methoxymethyl (MOM), the deprotection of compound 4 is performed via action of diluted acid in solvent of alcohol and water, wherein, the reaction condition is the common condition of this method.

The present invention also relates to an intermediate compound 4 of docetaxel, wherein, $R_1$ represents tert-butyl dimethyl silyl (TBS), triethylsilyl (TES), ethoxyethyl (EE), tetrahydropyranyl (THP), trichloroethoxycarbonyl (Troc) or methoxymethyl (MOM), trichloroethoxycarbonyl (Troc) or triethylsilyl (TES) is preferable.

The present invention further relates to a process for preparing compound 4, including the following steps: compound 4 is prepared by hydroxyl acylation reaction of compound 2 and 3.

Wherein, $R_1$ represents tert-butyl dimethyl silyl (TBS), triethylsilyl (TES), ethoxyethyl (EE), tetrahydropyranyl (THP), trichloroethoxycarbonyl (Troc) or methoxymethyl (MOM), trichloroethoxycarbonyl (Troc) or triethylsilyl (TES) is preferable.

Wherein, the method and condition of hydroxyl acylation reaction described may be the common method and condition of hydroxyl acylation reaction in the field. Preferably, the hydroxyl acylation reaction of compound 2 via the action of 4-dimethylamino-pyridine (DMAP) and triethylamine, or via the action of 4-dimethylamino-pyridine (DMAP) and N,N'-dicyclohexylcarbodiimide (DCC) with compound 3 in organic solvent. Wherein, the organic solvent is preferably one or several chosen from dichloromethane, ethyl acetate, toluene, diethyl ether, isopropyl ether, acetone, acetonitrile, tetrahydrofuran, methanol and ethanol. Toluene is a more preferably organic solvent. The volume/mass ratio of the solvent and compound 2 is preferably 5~20 ml/g. The usage of compound 3 is preferably 1~10 folds of the molar value of compound 2, more preferably 1.5~5 folds. The usage of 4-dimethylamino-pyridine (DMAP) is preferably 1.2~20 folds of the molar value of compound 2, more preferably 1.5~3 folds. The usage of triethylamine is preferably 1.2~20 folds of the molar value of compound 2, more preferably 3~5 folds. The usage of DCC is preferably 1.2~20 folds of the molar value of compound 2, more preferably 1.5~2 folds. The reaction is performed preferably at temperature between 0 and 100° C., more preferably at temperature between 20 and 50° C. The reaction time is preferably decided by detection of the completion of the reaction, usually 10~36 hours.

Figure 3:
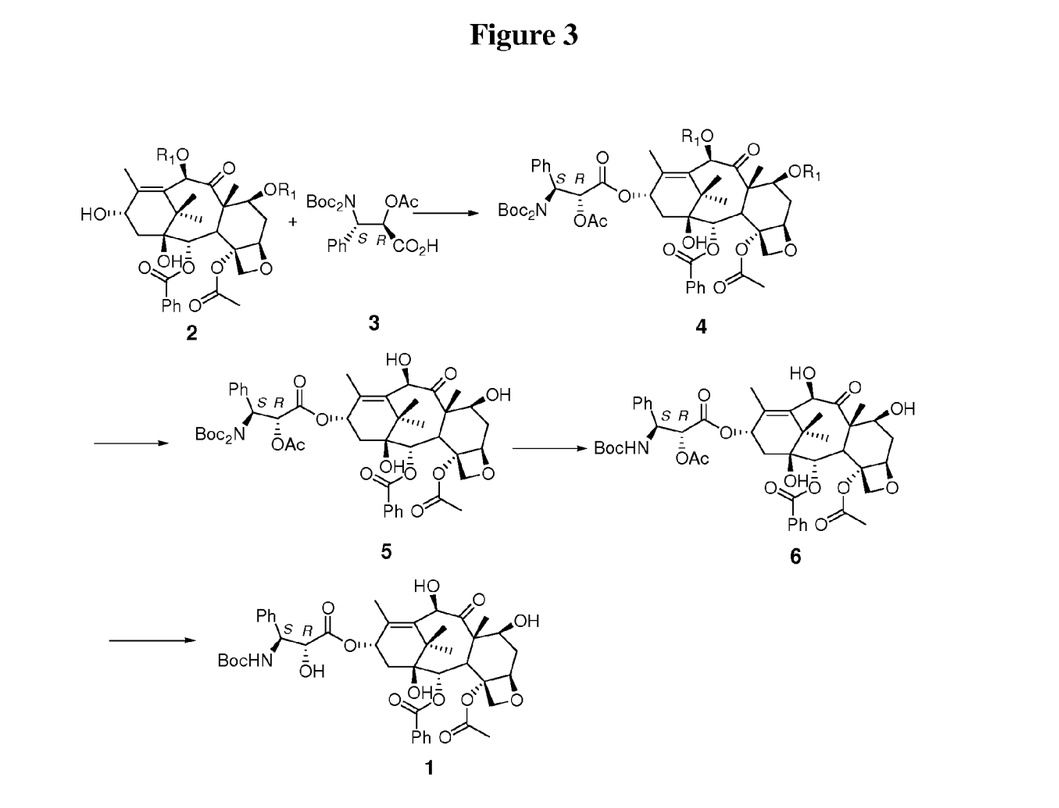
FIG. 3 shows a schema for making compound 1.

The best process for preparing docetaxel described in the present invention includes the following steps: 2+3→4→5→6→1 as shown in FIG. 3, in which:

a) hydroxyl acylation reaction of compound 2 and 3 to obtain compound 4, b) deprotection group R₁ of the hydroxyl group of compound 4 obtained from step a) to prepare compound 5, c) removing one tert-butoxycarbonyl of compound 5 obtained from step b) to prepare compound 6, d) removing one acetyl of compound 6 obtained from step c) to prepare compound 1.

Wherein, R₁ represents tert-butyl dimethyl silyl (TBS), triethylsilyl (TES), ethoxyethyl (EE), tetrahydropyranyl (THP), trichloroethoxycarbonyl (Troc) or methoxymethyl (MOM), trichloroethoxycarbonyl (Troc) or triethylsilyl (TES) is preferable, Boc is tert-butoxycarbonyl, Ac is acetyl, and Ph is phenyl.

Wherein, the method and condition related in every step are the same as described above.

The present invention also relates to intermediate compound 3 of docetaxel, wherein Boc is tert-butoxycarbonyl, Ac is acetyl, and Ph is phenyl.

3

The present invention further relates to a process for preparing compound 3, including the following steps: compound 3 was prepared from compound 9 by removing benzyl protection group of the hydroxyl group in organic solvent.

9

3

Wherein, Boc is tert-butoxycarbonyl, Ph is phenyl, Ac is acetyl, and Bn is benzyl.

Wherein, the method and condition of removing benzyl protection group of the hydroxyl group described may be the common method and condition of removing benzyl protection group of the hydroxyl group in the field. Preferably, the hydrogenation of compound 9 is performed via the action of palladium carbon. Wherein, the pressure is preferably 1~10 atm, the mass percentage of palladium in palladium carbon is preferably 1~20%, more preferably 2~10%. The usage of palladium carbon is preferably 0.01~0.5 folds of the mass of compound 9, more preferably 0.05~0.3 folds. The reaction is performed preferably at temperature between 0 and 60° C., more preferably at temperature between 10 and 30° C. The reaction time is decided by the detection of the completion of the reaction, usually 2~24 hours.

In the present invention, the compound 9 described may be prepared by the following method: compound 9 was prepared from compound 8 by the reaction of protecting amino group using tert-butoxycarbonyl group in organic solvent.

8

9

Wherein, Boc is tert-butoxycarbonyl, Ph is phenyl, Ac is acetyl, and Bn is benzyl.

Wherein, the method and condition of the reaction of protecting amino group using tert-butoxycarbonyl group described are the common method and condition of the reaction of protecting amino group using tert-butoxycarbonyl group in the field. Preferably, the reaction of compound 8 via the action of 4-dimethylamino-pyridine (DMAP) with di-t-butyl dicarbonate (Boc₂O) is performed. Wherein, the organic solvent is preferably one or several chosen from dichloromethane, ethyl acetate, toluene, diethyl ether, isopropyl ether, acetone, acetonitrile, and tetrahydrofuran. Acetonitrile is more preferably used. The volume/mass ratio of organic solvent and compound 8 is preferably 5~50 ml/g. The usage of 4-dimethylamino-pyridine is preferably 1~10 folds of the molar value of compound 8, more preferably 1.2~2.5 folds. The usage of di-t-butyl dicarbonate (Boc₂O) is preferably 1~10 folds of the molar value of compound 8, more preferably 2~5 folds. The reaction is performed preferably at temperature between 0 and 80° C., more preferably at temperature between 50 and 60° C. The reaction time is decided by the detection of the completion of the reaction, preferably 2~24 hours.

Wherein, the compound 8 may be prepared by the following method: compound 8 is prepared from compound 7 by acetylation of the hydroxyl group.

7

8

Wherein, Boc is tert-butoxycarbonyl, Ph is phenyl, Ac is acetyl, and Bn is benzyl.

Wherein, the method and condition of acetylation of the hydroxyl group described are the common method and condition of acetylation of the hydroxyl group in the field. Preferably, the acetylation of compound 7 is performed via the action of acetic anhydride in organic solvent. Wherein, the organic solvent is preferably one or several chosen from dichloromethane, ethyl acetate, toluene, diethyl ether, isopropyl ether, acetone, pyridine, acetonitrile, and tetrahydrofuran. Dichloromethane and/or pyridine are more preferably used. The volume/mass ratio of the solvent and compound 7 is preferably 5~50 ml/g, more preferably 5~10 ml/g. The usage of acetic anhydride is preferably 1~10 folds of the molar value of compound 7, more preferably 1.5~3 folds. The reaction is performed preferably at temperature between 0 and 60° C., more preferably at temperature between 0 and 25° C. The reaction time is decided by the detection of the completion of the reaction, preferably 2~12 hours.

The present invention also relates to the intermediate compound 9 of docetaxel, wherein Boc is tert-butoxycarbonyl, Ph is phenyl, Ac is acetyl, and Bn is benzyl.

9

The reagents and raw materials may be bought from the market, except where specially defined.

The advantages of the present invention are: the protective groups used in the preparation of the present invention are easy to be removed, the purification of each intermediate is easy, the cost is lower, the yield and the purity are higher, and the processes may be scaled to commercial implementation.

DETAILED DESCRIPTION OF THE INVENTION

The examples below are given as a nonlimiting illustration of the invention.

Wherein, 2a, 4a, 2b, and 4b in examples 3~9 are the same as those in examples 1 and 2.

Example 1

Step 1

2a

C$_{35}$H$_{38}$Cl$_6$O$_{14}$
Mol. Wt.: 895.38

3

C$_{21}$H$_{29}$NO$_8$
Mol. Wt.: 423.46

4a

C$_{56}$H$_{65}$Cl$_6$NO$_{21}$
Mol. Wt.: 1300.83

To a solution of compound 2a (50 g, 55.84 mmol) and compound 3 (50 g, 117.9 mmol) in dichloromethane (5000 mL), is added DMAP (10 g, 81.97 mmol) and triethylamine (100 mL, 722 mmol). The mixture is heated to 40° C. and stirred for 8 hours to the completion of the reaction. Then the mixture is filtered and dichloromethane is removed in vacuo. The residue is purified by column chromatography to obtain compound 4a (45 g, 62.0% yield).

$^1$H NMR (500 MHz, CDCl$_3$) δ: 8.08 (d, J=8.5 Hz, 2H), 7.68-7.14 (m, 8H), 6.20 (m, 1H), 6.01 (d, J=10.8 Hz, 1H), 5.88 (m, 1H), 5.62 (m, 2H), 5.55 (m, 1H), 4.96 (m, 1H), 4.90 (m, 1H), 4.75 (m, 2H), 4.58 (d, J=11.8 Hz, 1H), 4.29 (d, J=8.5 Hz, 1H), 4.12 (m, 1H), 4.03 (m, 1H), 3.84 (d, J=7.1 Hz, 1H), 3.48 (m, 2H), 2.54 (m, 1H), 2.45 (s, 3H), 2.21 (m, 1H), 2.17 (s, 3H), 1.89 (s, 3H), 1.80 (s, 3H), 1.59 (s, 9H), 1.45 (s, 9H), 1.25 (s, 3H), 1.21 (s, 3H).

Step 2

To a solution of compound 4a (40 g, 30.75 mmol) and acetic acid (500 mL, 8.74 mol) in 50% (v/v) methanol aqueous solution (100 mL), was added Zinc powder (50 g, 769 mmol). The mixture was heated under reflux (80° C.) for 1 h. Then the mixture was cooled and washed with saturated sodium bicarbonate to neutral. After the solvent was removed in vacuo, the residue is purified by column chromatography to obtain compound 5 (23 g, 78.9% yield) as a white solid.

$^1$H NMR (500 MHz, CDCl$_3$) δ: 8.11 (d, J=8.5 Hz, 2H), 7.60-7.13 (m, 8H), 6.28 (m, 1H), 6.11 (d, J=10.5 Hz, 1H), 5.78 (m, 1H), 5.65 (m, 1H), 4.88 (m, 1H), 4.80 (m, 1H), 4.63 (d, J=11.0 Hz, 1H), 4.26 (d, J=8.9 Hz, 1H), 4.08 (m, 1H), 4.00 (m, 1H), 3.85 (d, J=7.1 Hz, 1H), 3.55 (m, 2H), 2.56 (m, 1H), 2.43 (s, 3H), 2.16 (m, 1H), 2.10 (s, 3H), 1.86 (s, 3H), 1.77 (s, 3H), 1.58 (s, 9H), 1.40 (s, 9H), 1.23 (s, 3H), 1.18 (s, 3H).

Step 3

5

C$_{50}$H$_{63}$NO$_{17}$
Mol. Wt.: 950.03

6

C$_{45}$H$_{55}$NO$_{15}$
Mol. Wt.: 849.92

To a solution of compound 5 (23 g, 24.21 mmol) in dichloromethane (500 mL), was added 2 ml trifluoroacetic acid (3.08 g, 27.02 mmol). The mixture was stirred at 25° C. till the disappearance of the raw material. After the mixture was washed with saturated sodium bicarbonate, water, dried, and concentrated in vacuo, the residue was purified by column chromatography to give compound 6 (18 g, 87.5% yield) as a white solid.

$^1$H NMR (CDCl$_3$, 500M) δ: 8.10 (m, 1H), 7.62 (m, 2H), 7.48 (m, 2H), 7.36 (m, 5H), 6.20 (t, J=9.1 Hz, 1H), 5.65 (d, J=7.1 Hz, 1H), 5.48 (d, J=9.1 Hz, 1H), 5.25 (d, J=9.2 Hz, 1H), 5.20 (s, 1H), 4.96 (d, J=9.1 Hz, 1H), 4.64 (m, 1H), 4.30 (d, J=9.1 Hz, 1H), 4.24 (m, 1H), 4.18 (d, J=9.1 Hz, 1H), 3.94 (d, J=7.1 Hz, 1H), 2.56 (m, 1H), 2.45 (s, 3H), 2.39 (s, 3H), 2.26 (m, 2H), 1.87 (s, 3H), 1.76 (s, 3H), 1.34 (s, 9H), 1.24 (s, 3H), 1.10 (s, 3H);

Step 4

6

C$_{45}$H$_{55}$NO$_{15}$
Mol. Wt.: 849.92

1

C$_{43}$H$_{53}$NO$_{14}$
Mol. Wt.: 807.88

To a solution of compound 6 (15 g, 17.65 mmol) in tetrahydrofuran (500 mL), was added saturated sodium bicarbonate aqueous solution (50 ml), then added dropwisely 25 ml 30% hydrogen peroxide aqueous solution. The mixture was stirred at 25° C. till the disappearance of the raw material. After the excessive hydrogen peroxide was neutralized by diluted sodium sulfite aqueous solution, the mixture was extracted with dichloromethane, post processed in common way, and concentrated in vacuo. The residue was purified by column chromatography to give docetaxel (12 g, 84.4% yield) as a white solid.

m.p. 232-234° C.;

IR (KBr): 3400, 2900, 1710 cm$^{-1}$;

[α]$_D^{25}$: −36.2°;

$^1$H NMR (CDCl$_3$, 500M) δ: 8.12 (m, 1H), 7.60 (m, 2H), 7.50 (m, 2H), 7.38 (m, 5H), 6.22 (t, J=9.0 Hz, 1H), 5.68 (d, J=7.0 Hz, 1H), 5.46 (d, J=9.0 Hz, 1H), 5.26 (d, J=9.0 Hz, 1H), 5.22 (s, 1H), 4.94 (d, J=9.0 Hz, 1H), 4.62 (m, 1H), 4.32 (d, J=9.0 Hz, 1H), 4.26 (m, 1H), 4.19 (d, J=9.0 Hz, 1H), 3.91 (d, J=7.0 Hz, 1H), 2.58 (m, 1H), 2.37 (s, 3H), 2.28 (m, 2H), 1.88 (s, 3H), 1.75 (s, 3H), 1.35 (s, 9H), 1.23 (s, 3H), 1.11 (s, 3H);

$^{13}$C NMR (CDCl$_3$, 125M) δ211.1, 172.7, 170.3, 167.0, 155.5, 138.6, 138.5, 136.0, 133.0, 130.2, 129.3 128.7, 127.9, 127.4, 126.9, 84.4, 81.1, 80.2, 78.9, 77.3, 75.1, 74.5, 73.9, 72.3, 71.8, 57.7, 56.6, 46.6, 43.1, 36.7, 35.8, 28.2, 26.5, 22.5, 20.7, 14.3, 9.9.

Example 2

Step 1

C₄₁H₆₄O₁₀Si₂
Mol. Wt.: 773.11

C₂₁H₂₉NO₈
Mol. Wt.: 423.46

C₆₂H₉₁NO₁₇Si₂
Mol. Wt.: 1178.55

To a solution of compound 2b (50 g, 64.67 mmol) and compound 3 (50 g) in dichloromethane (5000 mL), is added DMAP (1 g) and DCC (100 g, 0.49 mol). The mixture is heated to 80° C. and stirred for 8 hours to the completion of the reaction. Then the mixture was filtered and dichloromethane was removed in vacuo. The residue was purified by column chromatography to give compound 4b (55 g, 72.1% yield).

$^1$H NMR (500 MHz, CDCl₃) δ: 8.18 (d, J=8.5 Hz, 2H), 7.88-7.30 (m, 8H), 6.26 (m, 1H), 6.01 (d, J=10.8 Hz, 1H), 5.85 (m, 1H), 5.58 (m, 1H), 4.96 (m, 1H), 4.88 (m, 1H), 4.56 (d, J=11.5 Hz, 1H), 4.25 (d, J=8.7 Hz, 1H), 4.18 (m, 1H), 4.05 (m, 1H), 3.85 (d, J=7.3 Hz, 1H), 3.45 (m, 2H), 2.56 (m, 1H), 2.44 (s, 3H), 2.21 (m, 1H), 2.17 (s, 3H), 1.89 (s, 3H), 1.80 (s, 3H), 1.59 (s, 9H), 1.45 (s, 9H), 1.25 (s, 3H), 1.21 (s, 3H), 0.97 (t, J=7.8 Hz, 9H), 0.95 (t, J=7.8 Hz, 9H), 0.68 (q, J=7.9 Hz, 6H), 0.65 (q, J=7.9 Hz, 6H).

Step 2

To a solution of compound 4b (50 g, 42.43 mmol) in tetrahydrofuran (2000 mL), is added 2N tetrabutylammonium fluoride solution (50 mL, 0.1 mol). The mixture is stirred overnight at room temperature (25° C.). After post procession in common way and evaporation of solvents, the residue is purified by column chromatography to give compound 5 (35 g, 86.9% yield), whose HNMR data is same as that of example 1.

Steps 3 and 4, together with identification data are the same as those of example 1.

Example 3

Step 1

To a solution of compound 2a (50 g, 55.84 mmol) and compound 3 (24 g, 55.84 mmol) in the mixture solvents of ethyl acetate (100 mL), methanol (100 mL), and acetonitrile (50 mL), is added DMAP (8.2 g, 67.00 mmol) and triethylamine (6.8 g, 67.00 mmol). The mixture is heated to 100° C. and stirred for 8 hours to the completion of the reaction. Then the mixture is filtered and the solvent is evaporated in vacuo. The residue is purified by column chromatography to give compound 4a (44.3 g, 61.0% yield).

Step 2

To a solution of compound 4a (40 g, 30.75 mmol) and acetic acid (9.2 g, 153.75 mmol) in the mixture solvents of water (50 mL), ethanol (50 mL), acetonitrile (50 mL), acetone (100 mL), is added Zinc powder (4 g, 61.5 mmol). The mixture was stirred at 0° C. until the completion of the reaction by TLC detection. Then the mixture is washed with saturated sodium bicarbonate to neutral. After the solvent was removed in vacuo, the residue was purified by column chromatography to give compound 5 (22.2 g, 75.9% yield) as a white solid.

Step 3

To a solution of compound 5 (23 g, 24.21 mmol) in ethyl acetate (80 mL) and acetonitrile (50 mL), is added trifluoroacetic acid (274 mg, 2.4 mmol). The mixture was stirred at 0° C. till disappearance of the raw material. After the mixture is washed with saturated sodium bicarbonate, water, and dried and concentrated in vacuo, the residue is purified by column chromatography to give compound 6 (18.9 g, 78% yield) as a white solid.

Step 4

To a solution of compound 6 (15 g, 17.65 mmol) in ethyl acetate (30 mL) and dichloromethane (45 mL), is added 0.5% (m/m) sodium bicarbonate aqueous solution (590 ml, 35.3 mmol), then added dropwisely 10% hydrogen peroxide aqueous solution (7 ml, 35.3 mmol). The mixture was stirred at 0° C. till disappearance of the raw material. After the excessive hydrogen peroxide is neutralized by diluted sodium sulfite aqueous solution, the mixture was extracted with dichloromethane, post processed in common way, and concentrated in vacuo. The residue is purified by column chromatography to give docetaxel (12 g, 84.4% yield) as a white solid.

Example 4

Step 1

To a solution of compound 2b (50 g, 64.67 mmol) and compound 3 (274 g, 646.7 mmol) in tetrahydrofuran (500 mL) and toluene (500 mL), is added DMAP (157 g, 1.29 mol) and DCC (157 g, 77.604 mmol). The mixture is heated to 40° C. and stirred until completion of the reaction by TLC detection. Then the mixture is filtered and solvent is removed in vacuo. The residue is purified by column chromatography to give compound 4b (52.6 g, 69% yield).

Step 2

To a solution of compound 4b (50 g, 42.43 mmol) in the mixture solvent of acetone (50 mL), acetonitrile (100 mL), methanol (100 mL), is added 2N tetrabutylammonium fluoride solution (50 mL, 0.1 mol). The mixture was stirred overnight at room temperature (25° C.). After post procession in common way and solvents evaporated, the residue is purified by column chromatography to give compound 5 (32.6 g, 80.9% yield), whose HNMR data is the same as that of example 1.

Step 3

To a solution of compound 5 (23 g, 24.21 mmol) in diethyl ether (230 mL) and isopropyl ether (230 mL), is added trifluoroacetic acid (5.5 g, 48.42 mmol). The mixture is stirred at 50° C. till disappearance of the raw material. After the mixture is washed with saturated sodium bicarbonate, water, and dried, and concentrated in vacuo, the residue is purified by column chromatography to give compound 6 (16 g, 78% yield) as a white solid.

Step 4

To a solution of compound 6 (15 g, 17.65 mmol) in diethyl ether (350 mL) and isopropyl ether (400 mL), is added 15% (m/m) sodium bicarbonate aqueous solution (100 ml, 176.5 mmol), then added dropwisely 70% hydrogen peroxide aqueous solution (5 ml, 176.5 mmol). The mixture was stirred at 50° C. till disappearance of the raw material. After the excessive hydrogen peroxide was neutralized by diluted sodium sulfite aqueous solution, the mixture was extracted with dichloromethane, post processed in common way, and concentrated in vacuo. The residue is purified by column chromatography to give docetaxel (11.4 g, 80% yield) as a white solid.

Example 5

Step 1

To a solution of compound 2a (50 g, 55.84 mmol) and compound 3 (50 g, 117.9 mmol) in the mixture solvent of diethyl ether (500 mL) and isopropyl ether (50 mL), and acetone (50 mL), is added DMAP (68 g, 558.4 mmol) and triethylamine (101 g, 1 mol). The mixture is heated to 100° C. and stirred for 8 hours till completion of the reaction. Then the mixture is filtered and solvent is evaporated in vacuo. The residue was purified by column chromatography to give compound 4a (44.3 g, 61.0% yield).

Step 2

To a solution of compound 4a (40 g, 30.75 mmol) in the mixture solvent of acetic acid (37 g, 615 mmol), water (50 mL), diethyl ether (240 mL), and tetrahydrofuran (240 mL), is added Zinc powder (39 g, 615 mmol). The mixture is stirred at 40° C. until completion of the reaction by TLC detection. Then the mixture is washed with saturated sodium bicarbonate to neutral. After the solvent is removed in vacuo, the residue is purified by column chromatography to give compound 5 (21.3 g, 73% yield) as a white solid.

Step 3

To a solution of compound 5 (23 g, 24.21 mmol) in tetrahydrofuran (299 mL), is added trifluoroacetic acid (274 mg, 2.4 mmol). The mixture was stirred at 0° C. till disappearance of the raw material. After the mixture was washed with saturated sodium bicarbonate, water, and dried and concentrated in vacuo, the residue is purified by column chromatography to give compound 6 (17.0 g, 78% yield) as a white solid.

Step 4

To a solution of compound 6 (15 g, 17.65 mmol) in acetone (30 mL) and acetonitrile (45 mL), was added 0.5% (m/m) sodium bicarbonate aqueous solution (1780 ml, 105.9 mmol), then added dropwisely 10% hydrogen peroxide aqueous solution (21 ml, 105.9 mmol). The mixture was stirred at 25° C. till disappearance of the raw material. After the excessive hydrogen peroxide was neutralized by diluted sodium sulfite aqueous solution, the mixture was extracted with dichloromethane, post processed in common way, and concentrated in vacuo. The residue was purified by column chromatography to give docetaxel (11.4 g, 80% yield) as a white solid.

Example 6

Step 1

To a solution of compound 2a (50 g, 55.84 mmol) and compound 3 (50 g, 117.9 mmol) in the mixture solvent of diethyl ether (500 mL) and isopropyl ether (50 mL), and acetone (50 mL), is added DMAP (68 g, 558.4 mmol) and triethylamine (101 g, 1 mol). The mixture is heated to 100° C. and stirred for 8 hours till completion of the reaction. Then the mixture is filtered and solvent is evaporated in vacuo. The residue is purified by column chromatography to give compound 4a (44.3 g, 61.0% yield).

Step 2

To a solution of compound 4a (40 g, 30.75 mmol) in the mixture solvents of acetic acid (12.9 g, 215.25 mmol) water (50 mL), dicholoromethane (200 mL), ethyl acetate (100 mL) and toluene (180 mL), is added Zinc powder (11.7 g, 184.5 mmol). The mixture is stirred at 40° C. until completion of the reaction by TLC detection. Then the mixture is washed with saturated sodium bicarbonate to neutral. After the solvent is removed in vacuo, the residue is purified by column chromatography to give compound 5 (21.3 g, 73% yield) as a white solid.

Step 3

To a solution of compound 5 (23 g, 24.21 mmol) in toluene (150 mL) and acetone (159 mL), is added trifluoroacetic acid (274 mg, 2.4 mmol). The mixture is stirred at 0° C. till disappearance of the raw material. After the mixture was washed with saturated sodium bicarbonate, water, and dried and concentrated in vacuo, the residue is purified by column chromatography to give compound 6 (17.0 g, 78% yield) as a white solid.

Step 4

To a solution of compound 6 (15 g, 17.65 mmol) in toluene (30 mL) and tetrahydrofuran (45 mL), is added 0.5% (m/m) sodium bicarbonate aqueous solution (1780 ml, 105.9 mmol), then added dropwisely 10% hydrogen peroxide aqueous solution (21 ml, 105.9 mmol). The mixture is stirred at 25° C. till disappearance of the raw material. After the excessive hydrogen peroxide is neutralized by diluted sodium sulfite aqueous solution, the mixture is extracted with dichloromethane, post processed in common way, and concentrated in vacuo. The residue is purified by column chromatography to give docetaxel (11.4 g, 80% yield) as a white solid.

Example 7

Step 1

To a solution of compound 2b (50 g, 64.67 mmol) and compound 3 (50 g) in tetrahydrofuran (500 mL) and toluene (500 mL), is added DMAP (157 g, 1.29 mol) and DCC (15.7 g, 77.604 mmol). The mixture is heated to 40° C. and stirred until completion of the reaction by TLC detection. Then the mixture is filtered and solvent is removed in vacuo. The residue is purified by column chromatography to give compound 4b (52.6 g, 69% yield).

Step 2

To a solution of compound 4b (50 g, 42.43 mmol) in the mixture solvents of ethyl acetate (300 mL), diethyl ether (400 mL) and isopropyl ether (300 mL), is added 2N tetrabutylammonium fluoride solution (21 mL, 42.43 mol). The mixture is stirred overnight at 0° C. After post procession in common way and solvents evaporated, the residue is purified by column chromatography to give compound 5 (32.6 g, 80.9% yield), whose HNMR data is the same as that of example 1.

Step 3

To a solution of compound 5 (23 g, 24.21 mmol) in toluene (2 mL), diethyl ether (2 mL) isopropyl ether (5 mL), acetone (5 mL), and dichloromethane (446 mL), is added trifluoroacetic acid (5.5 g, 48.42 mmol). The mixture is stirred at 50° C. till disappearance of the raw material. After the mixture is washed with saturated sodium bicarbonate, water, and dried and concentrated in vacuo, the residue is purified by column chromatography to give compound 6 (16 g, 78% yield) as a white solid.

Step 4

To a solution of compound 6 (15 g, 17.65 mmol) in toluene (5 mL), diethyl ether (5 mL), isopropyl ether (4 mL), acetone (5 mL), acetonitrile (5 mL), and dichloromethane (726 mL), is added 15% (m/m) sodium bicarbonate aqueous solution (100 ml, 176.5 mmol), then added dropwisely 70% hydrogen peroxide aqueous solution (5 ml, 176.5 mmol). The mixture is stirred at 50° C. till disappearance of the raw material. After the excessive hydrogen peroxide is neutralized by diluted sodium sulfite aqueous solution, the mixture was extracted with dichloromethane, post processed in common way, and concentrated in vacuo. The residue is purified by column chromatography to give docetaxel (11.4 g, 80% yield) as a white solid.

Example 8

Step 1

To a solution of compound 2b (50 g, 64.67 mmol) and compound 3 (50 g, 646.7 mmol) in tetrahydrofuran (500 mL) and toluene (500 mL), is added DMAP (157 g, 1.29 mol) and DCC (157 g, 77.604 mmol). The mixture is heated to 40° C. and stirred until completion of the reaction by TLC detection. Then the mixture is filtered and solvent is removed in vacuo. The residue is purified by column chromatography to give compound 4b (52.6 g, 69% yield).

Step 2

To a solution of compound 4b (50 g, 42.43 mmol) in the mixture solvent of toluene (500 mL) and ethanol (500 mL), is added 2N tetrabutylammonium fluoride solution (425 mL, 0.85 mol). The mixture is stirred overnight at 80° C. After post procession in common way and solvents evaporate, the residue is purified by column chromatography to give compound 5 (32.6 g, 80.9% yield), whose HNMR data is the same as that of example 1.

Step 3

To a solution of compound 5 (23 g, 24.21 mmol) in toluene (2 mL), diethyl ether (2 mL) isopropyl ether (5 mL), acetone (5 mL) and dichloromethane (446 mL) is added trifluoroacetic acid (5.5 g, 48.42 mmol). The mixture is stirred at 50° C. till the disappearance of the raw material. After the mixture is washed with saturated sodium bicarbonate, water, amd dried and concentrated in vacuo, the residue is purified by column chromatography to give compound 6 (16 g, 78% yield) as a white solid.

Step 4

To a solution of compound 6 (15 g, 17.65 mmol) in toluene (5 mL), diethyl ether (5 mL), isopropyl ether (4 mL), acetone (5 mL), acetonitrile (5 mL), and dichloromethane (726 mL), is added 15% (m/m) sodium bicarbonate aqueous solution (100 ml, 176.5 mmol), then added dropwisely 70% hydrogen peroxide aqueous solution (5 ml, 176.5 mmol). The mixture is stirred at 50° C. till disappearance of the raw material. After the excessive hydrogen peroxide is neutralized by diluted sodium sulfite aqueous solution, the mixture is extracted with dichloromethane, post processed in common way, and concentrated in vacuo. The residue is purified by column chromatography to give docetaxel (11.4 g, 80% yield) as a white solid.

Example 9

Step 1

To a solution of compound 2b (50 g, 64.67 mmol) and compound 3 (50 g) in tetrahydrofuran (500 mL) and toluene (500 mL), is added DMAP (157 g, 1.29 mol) and DCC (15.7 g, 77.604 mmol). The mixture is heated to 40° C. and stirred until completion of the reaction by TLC detection. Then the mixture is filtered and solvent is removed in vacuo. The residue is purified by column chromatography to give compound 4b (52.6 g, 69% yield).

Step 2

To a solution of compound 4b (50 g, 42.43 mmol) in the anhydrous tetrahydrofuran (600 mL), is added 2N tetrabutylammonium fluoride solution (212 mL, 424.3 mmol). The mixture was stirred overnight at 40° C. After post procession in common way and solvents evaporated, the residue is purified by column chromatography to give compound 5 (32.2 g, 80% yield), whose HNMR data is the same as that of example 1.

Step 3

To a solution of compound 5 (23 g, 24.21 mmol) in toluene (2 mL), diethyl ether (2 mL), isopropyl ether (5 mL), acetone (5 mL) and dichloromethane (446 mL) is added trifluoroacetic acid (5.5 g, 48.42 mmol). The mixture is stirred at 50° C. till disappearance of the raw material. After the mixture was washed with saturated sodium bicarbonate, water, and dried and concentrated in vacuo, the residue is purified by column chromatography to give compound 6 (16 g, 78% yield) as a white solid.

Step 4

To a solution of compound 6 (15 g, 17.65 mmol) in toluene (5 mL), diethyl ether (5 mL), isopropyl ether (4 mL), acetone (5 mL), acetonitrile (5 mL), and dichloromethane (726 mL), is added 15% (m/m) sodium bicarbonate aqueous solution (100 ml, 176.5 mmol) then added dropwisely 70% hydrogen peroxide aqueous solution (5 ml, 176.5 mmol). The mixture is stirred at 50° C. till disappearance of the raw material. After the excessive hydrogen peroxide is neutralized by diluted sodium sulfite aqueous solution, the mixture is extracted with dichloromethane, post processed in common way, and concentrated in vacuo. The residue was purified by column chromatography to give docetaxel (11.4 g, 80% yield) as a white solid.

Example 10 the Preparation of Compound 3

To a solution of (2R,3S)-benzyl-3-(tert-butoxycarbonylamino)-2-hydroxy-3-phenylpropionate (compound 7, 371 g, 1 mol) in anhydrous pyridine (500 mL), is added dropwisely acetic anhydride (200 ml, 2.1 mol). The mixture is stirred at 25~30° C. till disappearance of the raw material by TLC detection. The mixture is poured into the ice water (1000 mL), and pH value is adjudged to 5~6 by 6N hydrochloric acid. The water phase is extracted with ethyl acetate, the extracted liquid is washed with diluted hydrochloric acid, saturated sodium bicarbonate, saturated brine, anddried and the solvent is removed under pressure to get oil product. To the solution of the above oil product in acetonitrile (1 L), is added $Boc_2O$ (300 g, 1.38 mol) and 4-dimethylamino-pyridine (DMAP, 150 g). After completion of reaction by TLC detection, the acetonitrile is removed and the residue is purified by column chromatography to give oil product. To the solution of the above oil product in ethyl acetate, is added 5% palladium carbon (50 g). The hydrogenation reaction is performed at 3 atm hydrogen until hydrogen is not inhaled. The mixture is filtered and most of ethyl acetate is removed. The residue is added petroleum to precipitate product (350 g, 82.7% yield) as a white solid.

$^1H$ NMR (500 MHz, DMSO) δ: 13.26 (s, 1H), 7.40-7.30 (m, 5H), 5.80 (d, J=10.8 Hz, 1H), 5.53 (d, J=10.7 Hz, 1H), 2.07 (s, 3H), 1.36 (s, 18H).

Example 11 the Preparation of Compound 3

To a solution of (2R,3S)-benzyl-3-(tert-butoxycarbonylamino)-2-hydroxy-3-phenylpropionate (compound 7, 371 g, 1 mol) in acetone (500 mL), acetonitrile (500 mL), and tetrahydrofuran (855 mL), is added dropwise acetic anhydride (100 ml, 1 mol). The mixture is stirred at 0° C. tilldisappearance of the raw material by TLC detection. The mixture was poured into the ice water (1000 mL), and pH value was transferred to 5~6 by 6N hydrochloric acid. The water phase was extracted with ethyl acetate, the extracted liquid was washed with diluted hydrochloric acid, saturated sodium bicarbonate, saturated brine, dried and the solvent was removed under pressure to get oil product. To the solution of the above oil product in tetrahydrofuran (1000 mL) and acetone (1065 mL), was added $Boc_2O$ (218, 1 mol) and 4-dimethylamino-pyridine (DMAP, 122 g, 1 mol) at 0° C. After the completion of reaction by TLC detection, the solvent was removed and the residue was purified by column chromatography to give oil product. To the solution of the above oil product in ethyl acetate, was added 1% palladium carbon (5.14 g) at 0° C. The hydrogenation reaction was performed at 1 atm hydrogen until hydrogen is not inhaled. The mixture was filtered and most of ethyl acetate was removed. The residue was added petroleum to precipitate product (346 g, 81.7% yield) as a white solid.

Example 12 the Preparation of Compound 3

To a solution of (2R,3S)-benzyl-3-(tert-butoxycarbonylamino)-2-hydroxy-3-phenylpropionate (compound 7, 371 g, 1 mol) in dichloromethane (10 L), ethyl acetate (4 L), and toluene (4.55 L), was added dropwise acetic anhydride (1000 ml, 10 mol). The mixture was stirred at 60° C. till the disappearance of the raw material by TLC detection. The mixture was poured into the ice water (20 L), and pH value was transferred to 5~6 by 6N hydrochloric acid. The water phase was extracted with ethyl acetate, the extracted liquid was washed with diluted hydrochloric acid, saturated sodium bicarbonate, saturated brine, dried and the solvent was removed under pressure to get oil product. To the solution of the above oil product in dichloromethane (10 L), ethyl acetate (8 L), and toluene (2.65 L), was added $Boc_2O$ (2180, 10 mol) and 4-dimethylamino-pyridine (DMAP, 1220 g, 10 mol) at 80° C. After the completion of reaction by TLC detection, the solvent was removed and the residue was purified by column chromatography to give oil product. To the solution of the above oil product in ethyl acetate, was added 20% palladium carbon (256.5 g) at 60° C. The hydrogenation reaction was performed at 10 atm hydrogen until hydrogen is not inhaled. The mixture was filtered and most of ethyl acetate was removed. The residue was added petroleum to precipitate product (341.5 g, 80.7% yield) as a white solid.

Example 13 the Preparation of Compound 3

To a solution of (2R,3S)-benzyl-3-(tert-butoxycarbonylamino)-2-hydroxy-3-phenylpropionate (compound 7, 371 g, 1 mol) in diethyl ether (4000 mL) and isopropyl ether (4162 mL), was added dropwise acetic anhydride (500 ml, 5 mol). The mixture was stirred at 30° C. till the disappearance of the raw material by TLC detection. The mixture was poured into the ice water (1000 mL), and pH value was transferred to 5~6 by 6N hydrochloric acid. The water phase was extracted with ethyl acetate, the extracted liquid was washed with diluted hydrochloric acid, saturated sodium bicarbonate, saturated brine, dried and the solvent was removed under pressure to get oil product. To the solution of the above oil product in diethyl ether (4000 mL) and isopropyl ether (4086 mL), was added Boc$_2$O (1090, 5 mol) and 4-dimethylamino-pyridine (DMAP, 610 g, 5 mol) at 40° C. After the completion of reaction by TLC detection, the solvent was removed and the residue was purified by column chromatography to give oil product. To the solution of the above oil product in ethyl acetate, was added 10% palladium carbon (128.5 g) at 30° C. The hydrogenation reaction was performed at 6 atm hydrogen until hydrogen is not inhaled. The mixture was filtered and most of ethyl acetate was removed. The residue was added petroleum to precipitate product (338.6 g, 80% yield) as a white solid.

What is claimed is:

1. A process for preparing compound 6, including the following steps: compound 6 is prepared from compound 5 by removing one tert-butoxycarbonyl group:

5

6 wherein, Boc is tert-butoxycarbonyl, Ac is acetyl, and Ph is phenyl.

2. The process according to claim 1, wherein the process includes the following steps: the deprotection of compound 5 is performed via the action of trifluoroacetic acid in organic solvent;
wherein, the organic solvent is one or several chosen from dichloromethane, ethyl acetate, toluene, diethyl ether, isopropyl ether, acetone, acetonitrile, and tetrahydrofuran; the volume/mass ratio of the solvent and compound 5 is 5~20 ml/g; the usage of trifluoroacetic acid is 0.1~2 folds of the molar value of compound 5; the reaction is performed at temperature between 0 and 50° C.; The reaction time is decided by detection of the completion of the reaction.

3. An intermediate compound 5 of docetaxel,

5 wherein, Boc is tert-butoxycarbonyl, Ac is acetyl, and Ph is phenyl.

4. A process for preparing compound 5, including the following steps: compound 5 is prepared from compound 4 by removing protection group R$_1$ of the hydroxyl group,

4

5 wherein, R$_1$ represents tert-butyl dimethyl silyl, triethylsilyl, ethoxyethyl, tetrahydropyranyl, trichloroethoxycarbonyl or methoxymethyl.

5. The process according to claim 4, wherein the process includes the following steps:
where R$_1$ is trichloroethoxycarbonyl, the deprotection of compound 4 is performed via action of acetic acid and zinc in organic solvent and water; wherein, the organic solvent is one or several chosen from dichloromethane, ethyl acetate, toluene, diethyl ether, isopropyl ether, acetone, acetonitrile, tetrahydrofuran, methanol and ethanol; the volume/mass ratio of the solvent and compound 4 is 5~20 ml/g; the usage of acetic acid is 5~20 folds of the molar value of compound 4; the zinc is utilized in the form of zinc powder, the usage of which is 2~20 folds of the molar value of compound 4; the reaction is performed at temperature between 0 and 80° C.; the reaction time is decided by detection of the completion of the reaction;

where $R_1$ is triethylsilyl, the deprotection of compound 4 is performed via action of tetrabutylammonium fluoride in organic solvent; wherein, the organic solvent is one or several chosen from dichloromethane, ethyl acetate, toluene, diethyl ether, isopropyl ether, acetone, acetonitrile, tetrahydrofuran, methanol, and ethanol; the volume/mass ratio of the solvent and compound 4 is 5~20 ml/g; the usage of tetrabutylammonium fluoride is 1~20 folds of the molar value of compound 4; the reaction is performed at the temperature between 0 and 80° C.; the reaction time is decided by detection of the completion of the reaction;

where $R_1$ is tert-butyl dimethyl silyl, the deprotection of compound 4 is performed via action of tetrabutylammonium fluoride in organic solvent, wherein, the reaction condition is the common condition of this method;

where $R_1$ is ethoxyethyl, the deprotection of compound 4 is performed via action of diluted acid in solvent of alcohol and water, wherein, the reaction condition is the common condition of this method;

where $R_1$ is tetrahydropyranyl, the deprotection of compound 4 is performed via action of diluted acid in solvent of alcohol and water, wherein, the reaction condition is the common condition of this method;

where $R_1$ is methoxymethyl, the deprotection of compound 4 is performed via action of diluted acid in solvent of alcohol and water, wherein, the reaction condition is the common condition of this method.

6. An intermediate compound 4 of docetaxel,

4 wherein, $R_1$ represents tert-butyl dimethyl silyl, triethylsilyl, ethoxyethyl, tetrahydropyranyl, trichloroethoxycarbonyl or methoxymethyl.

7. A process for preparing compound 4, including the following steps: compound 4 is prepared by hydroxyl acylation reaction of compound 2 and 3,

2

+

3

-continued

4 wherein, $R_1$ represents tert-butyl dimethyl silyl, triethylsilyl, ethoxyethyl, tetrahydropyranyl, trichloroethoxycarbonyl or methoxymethyl.

8. The process according to claim 7, wherein the process includes the following steps:

the hydroxyl acylation reaction of compound 2 and 3 is performed via action of 4-dimethylamino-pyridine and triethylamine, or 4-dimethylamino-pyridine and N,N'-dicyclohexylcarbodiimide in organic solvent; wherein, the organic solvent is one or several chosen from dichloromethane, ethyl acetate, toluene, diethyl ether, isopropyl ether, acetone, acetonitrile, tetrahydrofuran, methanol and ethanol; the volume/mass ratio of the solvent and compound 2 is 5~20 ml/g; the usage of compound 3 is 1~10 folds of the molar value of compound 2; the usage of 4-dimethylamino-pyridine is 1.2~20 folds of the molar value of compound 2; the usage of triethylamine is 1.2~20 folds of the molar value of compound 2; the usage of N,N'-dicyclohexylcarbodiimide is 1.2~20 folds of the molar value of compound 2; the reaction is performed at temperature between 0 and 100° C.; the reaction time is decided by detection of the completion of the reaction.

9. A process for preparing docetaxel 1, including the following steps:

a) hydroxyl acylation reaction of compound 2 and 3 to obtain compound 4,
b) deprotection group $R_1$ of the hydroxyl group of compound 4 obtained from step a) to prepare compound 5,
c) removing one tert-butoxycarbonyl of compound 5 obtained from step b) to prepare compound 6,
d) removing one acetyl of compound 6 obtained from step c) to prepare compound 1;
wherein, $R_1$ represents tert-butyl dimethyl silyl, triethylsilyl, ethoxyethyl, tetrahydropyranyl, trichloroethoxycarbonyl or methoxymethyl, Boc is tert-butoxycarbonyl, Ac is acetyl, and Ph is phenyl.

10. An intermediate compound 3 of docetaxel;

wherein, Boc is tert-butoxycarbonyl, Ac is acetyl, and Ph is phenyl.

11. A process for preparing compound 3, including the following steps: compound 3 is prepared from compound 9 by removing benzyl protection group of the hydroxyl group in organic solvent;

wherein, Boc is tert-butoxycarbonyl, Ph is phenyl, Ac is acetyl, and Bn is benzyl.

12. The process according to claim 11, wherein the process includes the following steps:
the hydrogenation of compound 9 is performed via action of palladium carbon;
wherein, the pressure is 1~10 atm, the mass percentage of palladium in palladium carbon is 1~20%; the usage of palladium carbon is 0.01~0.5 folds of the mass of compound 9; the reaction is performed at temperature between 0 and 50° C.; the reaction time is decided by detection of the completion of the reaction.

13. The process according to claim 11, characterized in that compound 9 is prepared from compound 8 by reaction of protecting amino group using tert-butoxycarbonyl group in organic solvent;

wherein, Boc is tert-butoxycarbonyl, Ph is phenyl, Ac is acetyl, and Bn is benzyl.

14. The process according to claim 13, wherein compound 9 is prepared by the following method: reaction of compound 8 and di-t-butyl dicarbonate is performed via the action of 4-dimethylamino-pyridine;
wherein, the organic solvent is one or several chosen from dichloromethane, ethyl acetate, toluene, diethyl ether, isopropyl ether, acetone, acetonitrile, and tetrahydrofuran; the volume/mass ratio of the solvent and compound 8 is 5~50 ml/g; the usage of 4-dimethylamino-pyridine is 1~10 folds of the molar value of compound 8; the usage of di-t-butyl dicarbonate is 1~10 folds of the molar value of compound 8; the reaction is performed at temperature between 0 and 80° C.; the reaction time is decided by detection of the completion of the reaction.

15. The process according to claim 13, wherein compound 8 is prepared from compound 7 by acetylation of the hydroxyl group;

wherein, Boc is tert-butoxycarbonyl, Ph is phenyl, Ac is acetyl, and Bn is benzyl.

16. The process according to claim 15, wherein compound 8 is prepared by the following method: acetylation of compound 7 is performed via the action of acetic anhydride in organic solvent;

wherein, the organic solvent is one or several chosen from dichloromethane, ethyl acetate, toluene, diethyl ether, isopropyl ether, acetone, pyridine, acetonitrile, and tetrahydrofuran; the volume/mass ratio of the solvent and compound 7 is 5~50 ml/g; the usage of acetic anhydride is 1~10 folds of the molar value of compound 7; the reaction is performed at the temperature between 0 and 60° C.; the reaction time is decided by the detection of the completion of the reaction.

17. An intermediate compound 9 of docetaxel;

wherein, Boc is tert-butoxycarbonyl, Ph is phenyl, Ac is acetyl, and Bn is benzyl.

18. A process for preparing docetaxel 1, including the following steps:
step 1: compound 6 is prepared from compound 5 by removing one tert-butoxycarbonyl group;
step 2: compound 1 is prepared from compound 6 by removing one acetyl group;

wherein Boc is tert-butoxycarbonyl, Ac is acetyl, and Ph is phenyl.

19. The process according to claim 18, wherein the process of step 1 includes the following steps:
the deprotection of compound 5 is performed via the action of trifluoroacetic acid in organic solvent;
wherein the organic solvent is one or more solvents chosen from dichloromethane, ethyl acetate, toluene, diethyl ether, isopropyl ether, acetone, acetonitrile, and tetrahydrofuran;
the volume/mass ratio of the solvent and compound 5 is 5~20 ml/g;
the usage of trifluoroacetic acid is 0.1~2 folds of the molar value of compound 5;
the reaction is performed at temperature between 0 and 50° C.; and
the reaction time is decided by detection of the completion of the reaction.

20. The process according to claim 18, wherein the process of step 2 includes the following steps:
the deacetylation of compound 6 is performed via the action of hydrogen peroxide and sodium bicarbonate in organic solvent;
wherein the organic solvent is one or more solvents chosen from dichloromethane, ethyl acetate, toluene, diethyl ether, isopropyl ether, acetone, acetonitrile, and tetrahydrofuran;
the volume/mass ratio of the solvent and compound 6 is 5~50 ml/g;
the sodium bicarbonate is utilized in the form of 0.5%~saturated aqueous solution;
the usage of sodium bicarbonate is 2~10 folds of the molar value of compound 6;
hydrogen peroxide is utilized in the form of hydrogen peroxide aqueous solution, its mass percentage is 10~70%;
the usage of hydrogen peroxide is 2~10 folds of the molar value of compound 6; the reaction is performed at temperature between 0 and 50° C.; and
the reaction time is decided by detection of the completion of the reaction.

* * * * *